United States Patent
Bi et al.

(10) Patent No.: US 10,669,579 B2
(45) Date of Patent: Jun. 2, 2020

(54) DNA SEQUENCING WITH STACKED NANOPORES

(71) Applicant: INTERNATIONAL BUSINESS MACHINES CORPORATION, Armonk, NY (US)

(72) Inventors: Zhenxing Bi, Niskayuna, NY (US); Kangguo Cheng, Schenectady, NY (US); Juntao Li, Cohoes, NY (US); Xin Miao, Guilderland, NY (US)

(73) Assignee: International Business Machines Corporation, Armonk, NM (US)

( * ) Notice: Subject to any disclaimer, the term of this patent is extended or adjusted under 35 U.S.C. 154(b) by 33 days.

(21) Appl. No.: 15/211,552

(22) Filed: Jul. 15, 2016

(65) Prior Publication Data

US 2018/0016629 A1   Jan. 18, 2018

(51) Int. Cl.
*C12Q 1/6869* (2018.01)
*G01N 33/487* (2006.01)
*G01N 27/447* (2006.01)

(52) U.S. Cl.
CPC ..... *C12Q 1/6869* (2013.01); *G01N 27/44791* (2013.01); *G01N 33/48721* (2013.01)

(58) Field of Classification Search
CPC ............ C12Q 1/6869; C12Q 2565/631; B05D 1/005; B05D 1/02; C23C 16/50; C23F 1/00; G01N 27/44791; G01N 33/48721; B82Y 40/00; B01L 2300/0896
USPC ...................................................... 422/400
See application file for complete search history.

(56) References Cited

U.S. PATENT DOCUMENTS

| | | | |
|---|---|---|---|
| 8,652,779 B2 | 2/2014 | Turner et al. | |
| 8,794,054 B2 | 8/2014 | Gridelet et al. | |
| 8,828,138 B2 | 9/2014 | Bedell et al. | |
| 8,986,928 B2 | 3/2015 | Turner et al. | |
| 8,993,234 B2 | 3/2015 | Turner et al. | |
| 9,285,339 B2 | 3/2016 | Afzali-Ardakani et al. | |
| 2008/0254995 A1 | 10/2008 | Kim et al. | |
| 2011/0217763 A1* | 9/2011 | Rasooly | G01N 33/5438 435/287.1 |
| 2012/0060589 A1* | 3/2012 | Gridelet | G01N 33/5438 73/61.61 |
| 2012/0146162 A1* | 6/2012 | Cho | B82Y 40/00 257/414 |
| 2012/0193237 A1* | 8/2012 | Afzali-Ardakani | B82Y 15/00 204/627 |
| 2015/0028845 A1* | 1/2015 | Zhu | G01N 27/3275 324/71.5 |

(Continued)

FOREIGN PATENT DOCUMENTS

| | | | |
|---|---|---|---|
| WO | WO 2013016486 | * | 1/2013 |
| WO | 2015/176034 A1 | | 11/2015 |
| WO | 2016/049657 A1 | | 3/2016 |

OTHER PUBLICATIONS

Bai et al. (Nanoscale, 2014, 6, 8900-8906 (Year: 2014).*

*Primary Examiner* — Sally A Merkling
(74) *Attorney, Agent, or Firm* — Tutunjian & Bitetto, P.C.; Vazken Alexanian

(57) ABSTRACT

A sensing device includes a stack of dielectric layers having conductive materials disposed between the dielectric layers. A nanopore is disposed through the stacks of dielectric layers and separates the conductive materials to provide electrodes on opposite sides of the nanopore. Contacts connect to each of the electrodes.

20 Claims, 7 Drawing Sheets

(56) References Cited

U.S. PATENT DOCUMENTS

2015/0028846 A1    1/2015  Zhu
2015/0377830 A1*  12/2015  Baldauf ............... C12Q 1/6827
                                                              204/451

* cited by examiner

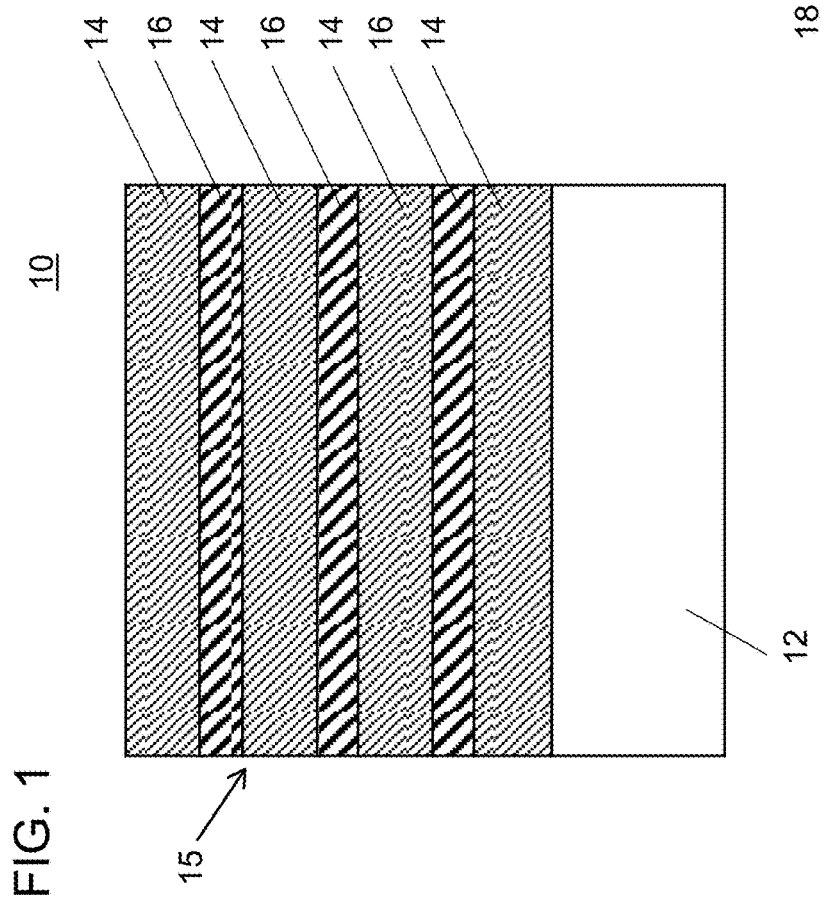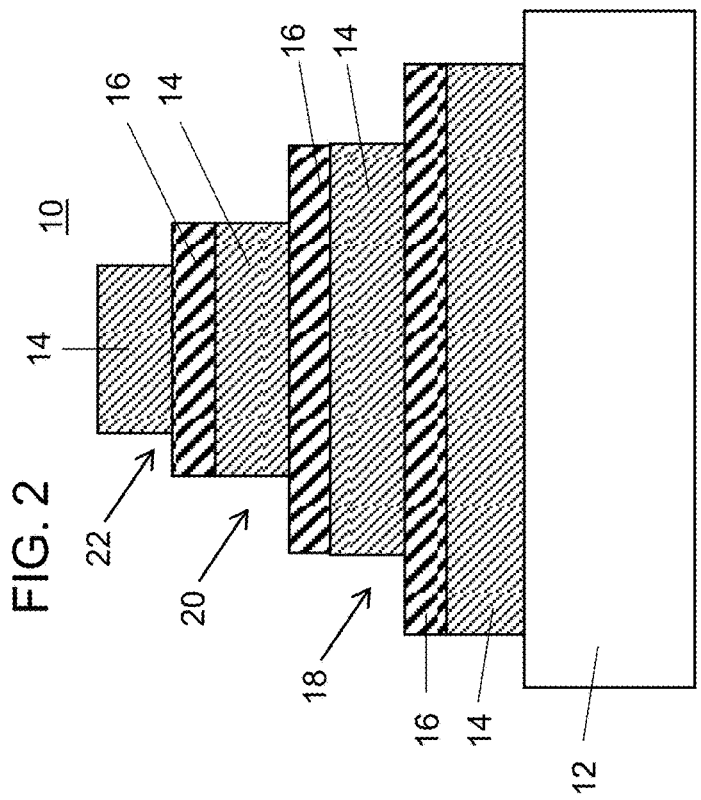

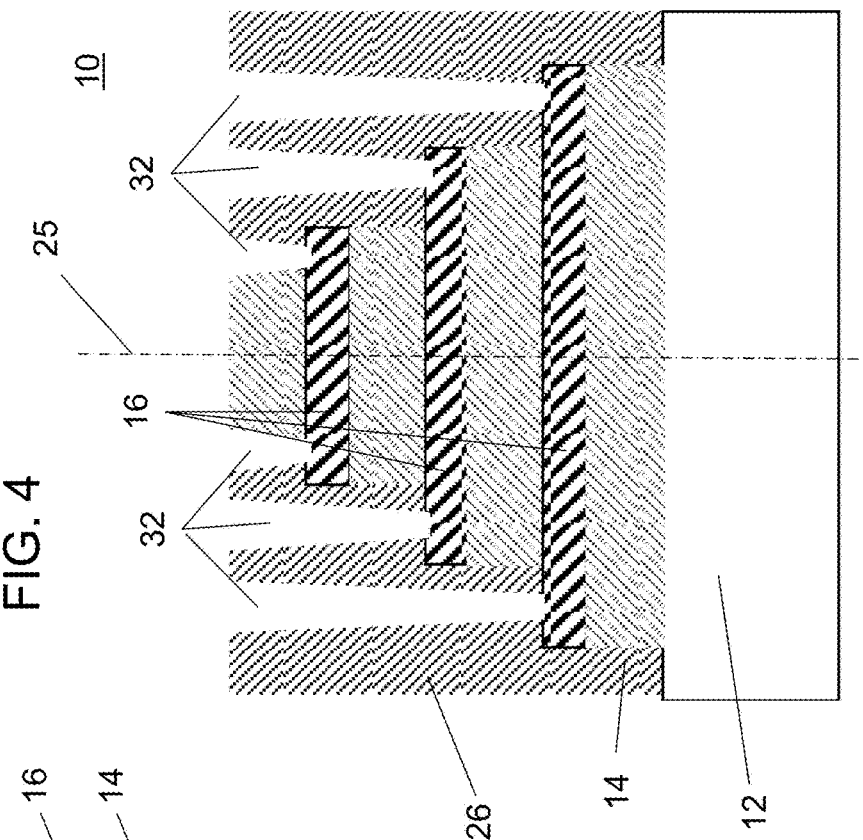
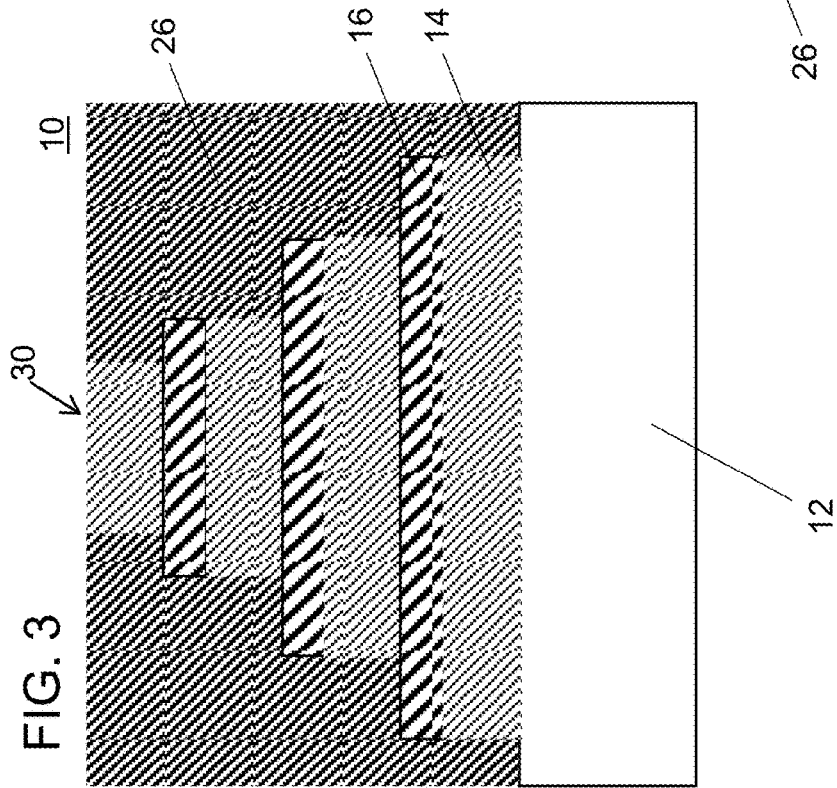

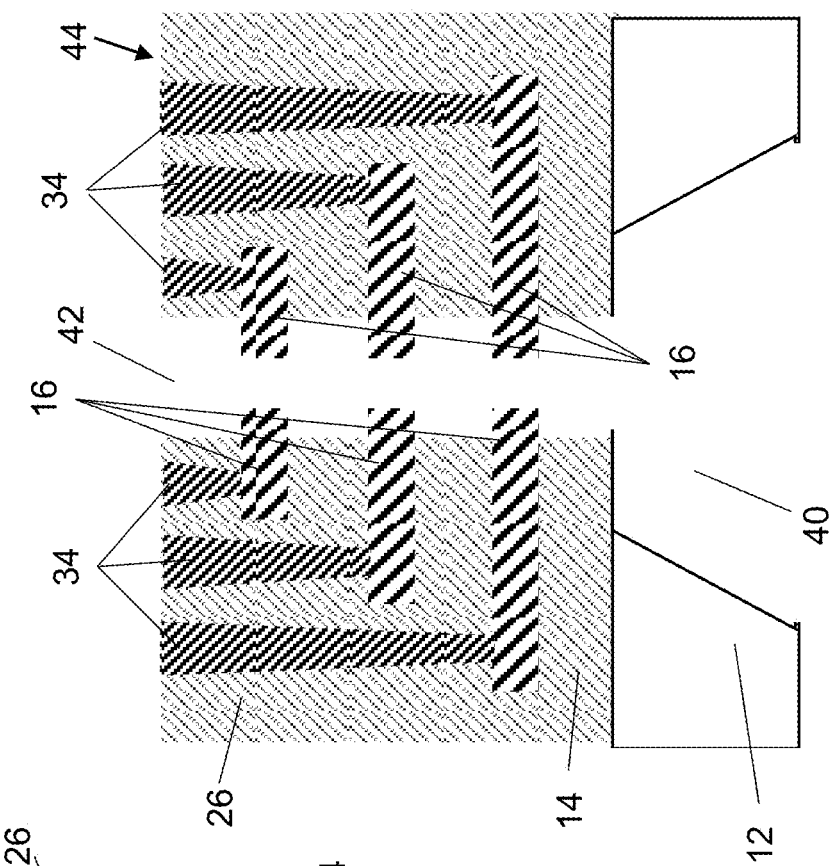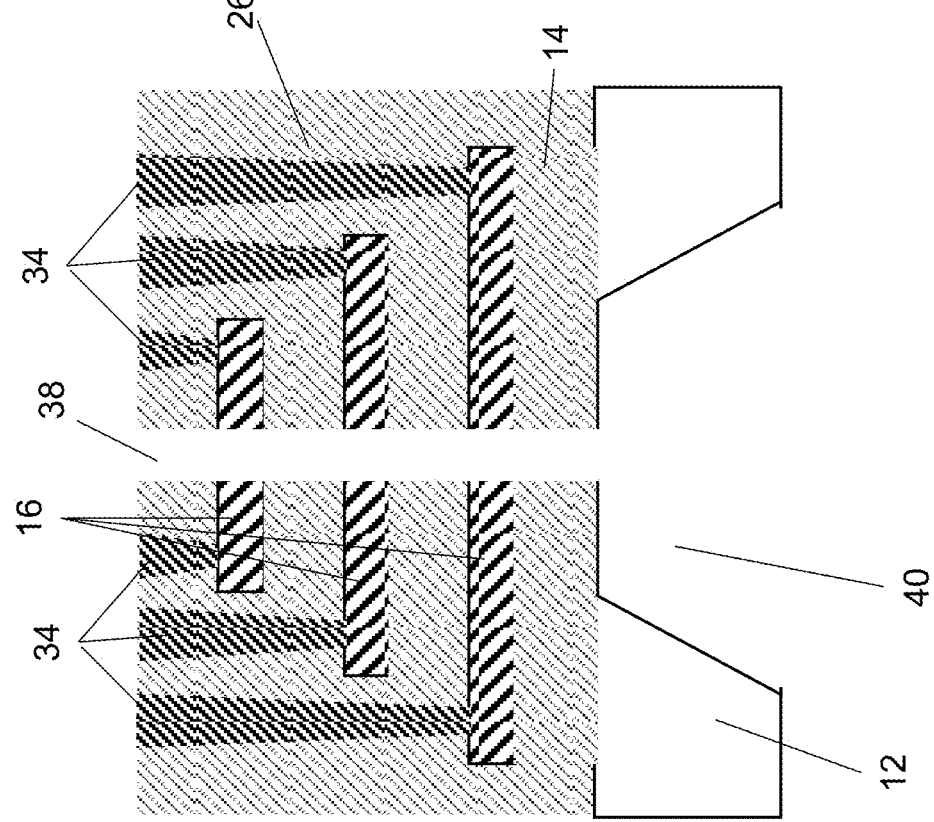

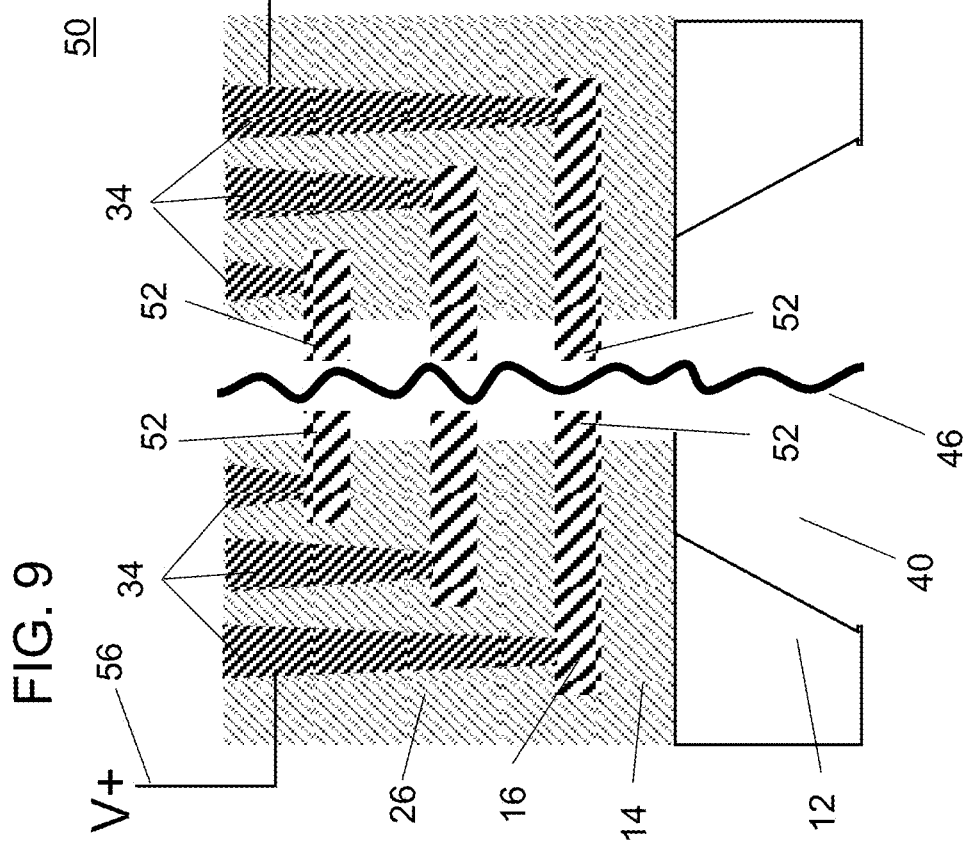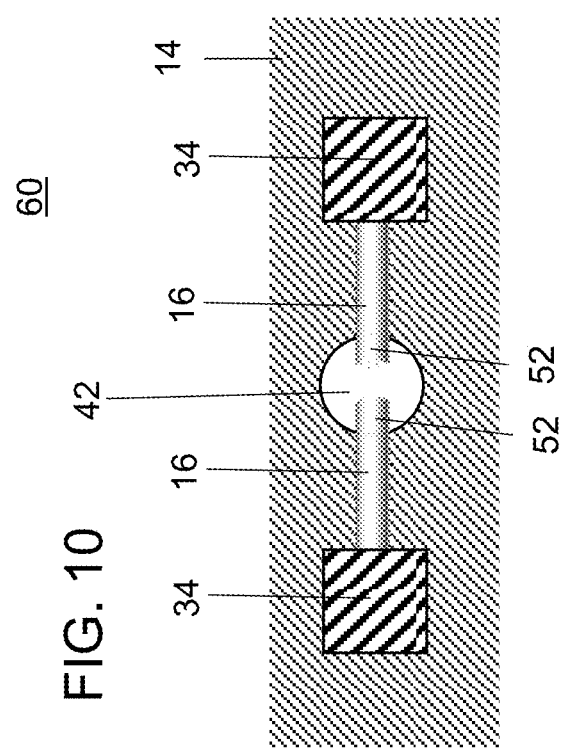

DNA SEQUENCING WITH STACKED NANOPORES

BACKGROUND

Technical Field

The present invention generally relates to molecular sensing, and more particularly to systems, devices and methods for use and fabrication of a nanopore stack for measuring molecules.

Description of the Related Art

Deoxyribose nucleic acid (DNA) sequencing includes processes for determining a precise order of nucleotides within a DNA molecule. Sequencing may include any method or technology that is employed to determine the order of four bases: adenine, guanine, cytosine, and thymine in a strand of DNA. Knowledge of DNA sequences is important for research, and plays an important role in many fields such as medical, biotechnology, forensics, virology and biological systematics.

SUMMARY

In accordance with an embodiment of the present principles, a sensing device includes a stack of dielectric layers having conductive materials disposed between the dielectric layers. A nanopore is disposed through the stacks of dielectric layers and separates the conductive materials to provide electrodes on opposite sides of the nanopore. Contacts connect to each of the electrodes.

Another sensing device includes a stack of dielectric layers having conductive lines disposed between the dielectric layers, the stack of dielectric layers being formed on a substrate. A nanopore is disposed through the stack of dielectric layers and separates the conductive lines to provide electrodes on opposite sides of the nanopore, wherein the electrodes form two or more electrode pairs and each electrode pair forms a sensor for measuring tunneling current changes when a molecule is present between the electrodes. Contacts connect to each of the electrodes.

A method for fabricating a stacked nanopore includes forming a stack of layers having alternating conductive lines and dielectric layers on a substrate; patterning the stack to form a staircase structure with the conductive lines having a length gradually changing at each level in the stack; depositing and planarizing a dielectric material over the staircase structure; forming contacts through the dielectric material to the conductive lines for each level of conductive lines; etching a nanopore through the stack of layers to form pairs of opposing electrodes across the nanopore using the conductive lines; and opening up the substrate to expose the nanopore.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein:

FIG. 1 is a cross-sectional view showing a stack of dielectric layers having conductive materials disposed between the dielectric layers in accordance with the present principles;

FIG. 2 is a cross-sectional view showing the stack of dielectric layers having conductive materials patterned to form a staircase structure in accordance with the present principles;

FIG. 3 is a cross-sectional view showing the staircase structure buried in a dielectric material and planarized to level a top surface in accordance with the present principles;

FIG. 4 is a cross-sectional view showing the dielectric material patterned to form contact openings in accordance with the present principles;

FIG. 7 is a cross-sectional view showing the nanopore opened up by etching the substrate in accordance with the present principles;

FIG. 8 is a cross-sectional view showing the nanopore further etched to form extended electrode tips on opposite sides of the nanopore in accordance with the present principles;

FIG. 9 is a cross-sectional view showing the device of FIG. 8 having a molecule within the nanopore in accordance with the present principles;

FIG. 10 is a top down view showing the device of FIG. 9 having tips of electrodes extending into the nanopore in accordance with the present principles;

DETAILED DESCRIPTION

Figure 5:
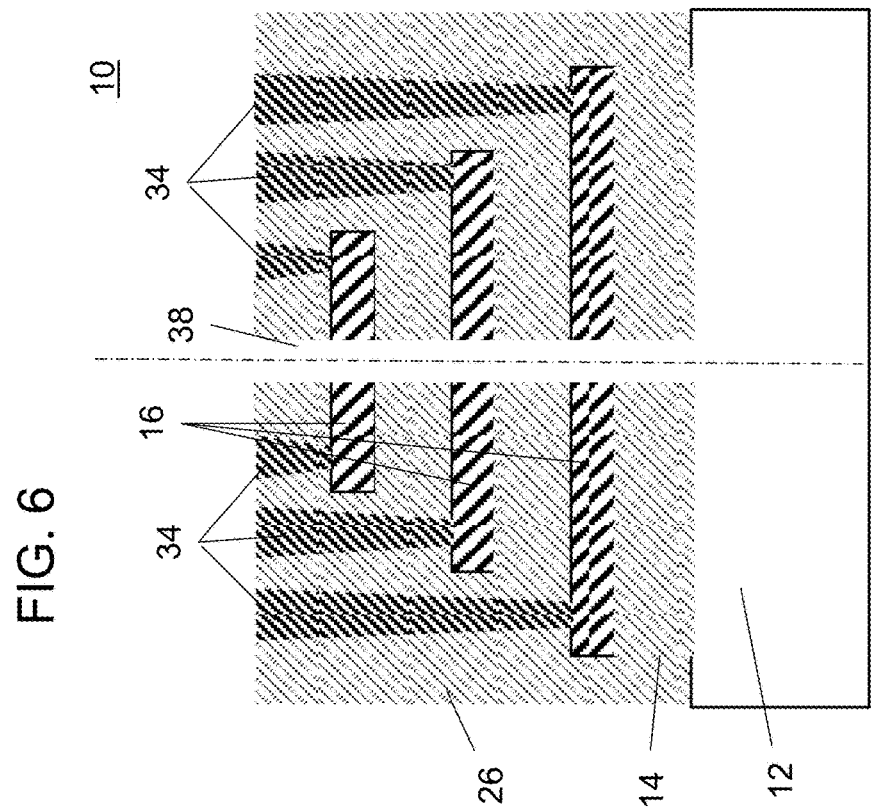
FIG. 5 is a cross-sectional view showing the contact openings filled with a conductive material and planarized to form contacts in accordance with the present principles.

In accordance with the present principles, methods and structures for forming stacked nanopores are provided. The stacked nanopores may have a plurality of applications. In one embodiment, for example, nanopores may be employed for deoxyribose nucleic acid (DNA) sequencing, ribonucleic acid (RNA) sequencing, analysis of proteins, viruses, etc. In one useful embodiment, nanopores are employed to perform parallel DNA sequencing to improve sequencing speed and accuracy.

The present principles provide a nanopore with sharp conductive tips on opposite sides of the nanopore. One tip is grounded and the other tip is biased with a positive voltage (V+). When DNA passes the nanopore, it changes the tunneling current between the two conductor tips. Different DNA nucleobases cause different changes in the tunneling current. The stacked nanopore provides multiple nanopore stacks isolated by an insulator (e.g., an oxide). When DNA passes through the nanopore stack, the tunneling current of each nanopore layer is recorded. This senses the DNA molecules multiple times (e.g., equal to the number of layers in the nanopore stack) in a single pass. Signals can then be averaged to minimize any variation due to the non-uniformity of the nanopore.

It is to be understood that the present invention will be described in terms of a given illustrative architecture; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The present embodiments may include a design for an integrated circuit chip, which may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements may be included in the compound and still function in accordance with the present principles. The compounds with additional elements will be referred to herein as alloys.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, may be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device may be otherwise oriented (rotated 90 degrees or at other orientations), and the spatially relative descriptors used herein may be interpreted accordingly. In addition, it will also be understood that when a layer is referred to as being "between" two layers, it can be the only layer between the two layers, or one or more intervening layers may also be present.

It will be understood that, although the terms first, second, etc. may be used herein to describe various elements, these elements should not be limited by these terms. These terms are only used to distinguish one element from another element. Thus, a first element discussed below could be termed a second element without departing from the scope of the present concept.

Referring now to the drawings in which like numerals represent the same or similar elements and initially to FIG. 1, a cross-sectional view for a partially fabricated integrated circuit device 10 is shown in accordance with one illustrative embodiment. The device 10 includes a substrate 12, which may include any suitable substrate material. including, e.g., a semiconductor material, a dielectric material, a ceramic material, a metal, etc. In useful embodiments, the substrate 12 may include silicon, germanium, quartz, glass, ceramic, silicon oxide, silicon nitride, etc. In particularly useful embodiments, the substrate 12 includes a material that is etch resistant during the formation of other structures on the device 10.

A stack 15 of layers is formed on the substrate 12. The stack 15 of layers may include an alternating pattern of dielectric layers 14 and conductive layers 16. The number of layers and their thicknesses can be determined based upon a depth needed to measure a molecule through the depth of the device. The number of alternating layer sets will also determine the number of conductive sensor pairs that will be employed to make the sensor measurements on the molecule. The dielectric layers 14 may include any suitable dielectric materials.

For example, the material for the dielectric layers 14 may be selected from the group consisting of silicon-containing materials such as amorphous silicon (a-Si, a-Si:H), silicon oxide ($SiO_2$), silicon nitride (SiN, SiON, SiBN, SiCBN), silicon carbide (SiC, SiCH, SiCO, SiCOH) and compounds; the above-mentioned silicon-containing materials with some or all of the Si replaced by Ge; carbon-doped oxides; inorganic oxides; inorganic polymers; hybrid polymers; organic polymers such as polyamides or SiLK™; other carbon-containing materials; organo-inorganic materials such as spin-on glasses and silsesquioxane-based materials; and diamond-like carbon (DLC, also known as amorphous hydrogenated carbon, a-C:H) with or without one or more additives selected from the group containing F, N, O, Si, Ge, metals and nonmetals. Additional choices for one or more of the dielectrics include: any of the aforementioned materials in porous form, or in a form that changes during processing to or from being porous and/or permeable to being non-porous and/or non-permeable. Dielectric layers 14 may also be mixtures, multilayers, or layered combinations of the aforementioned materials.

The conductive layers 16 may include any suitable conductive material, such as polycrystalline or amorphous silicon, a metal (e.g., tungsten, titanium, tantalum, ruthenium, zirconium, cobalt, copper, aluminum, lead, platinum, tin, silver, gold), a conducting metallic compound material (e.g., tantalum nitride, titanium nitride, tungsten silicide, tungsten nitride, ruthenium oxide, cobalt silicide, nickel silicide), carbon nanotube, conductive carbon, graphene, or any suitable combination of these materials. The conductive material may further comprise dopants that are incorporated during or after deposition.

The illustrative example shows three conductive layers 16 and four dielectric layers 14. It should be understood that the number of conductive layers 16 and dielectric layers 14 may be greater than or less than the number depicted and illustratively described. In one embodiment, the substrate 12 may include a semiconductor substrate, and the substrate 12 may include other components thereon. For example, the substrate 12 may include transistors, capacitors, logic devices, etc. In a particularly useful embodiment, the substrate 12 includes sensing circuits formed thereon for sensing the currents, data processing, storage, etc. caused by the presence of a molecule passing through a nanopore or other function, as will be described herein.

It should be understood that the conductive layers or conductors 16 may be patterned to form nanowires or fins before forming a corresponding dielectric layer 14 thereon. The conductive layers 16 may include thicker portions where contacts will be formed in later steps. The dielectric layers 14 may be formed of the same material, of different materials: or some of the dielectric layers 14 may be the same and some different. The dielectric layers 14 may be formed by various methods, including, but not limited to: spinning from solution, spraying from solution, chemical vapor deposition (CVD), plasma enhanced CVD (PECVD), sputter deposition, reactive sputter deposition, ion-beam deposition, evaporation, atomic layer deposition (ALD), etc. The conductive layers 16 may be formed by CVD, plasma-assisted CVD, high-density chemical vapor deposition (HD-CVD), plating, sputtering, evaporation, chemical solution deposition, ALD, etc.

Referring to FIG. 2, a staircase structure is formed by patterning/etching the dielectric layers 14 and the conductive layers 16 to form steps 18, 20 and 22 in the staircase structure. The pattern may be provided using resist masks (not shown) and lithography. The etch process may include a reactive ion etch (RIE). The etch chemistry may be changed to etch through both the dielectric layer 14 and the conductive layer 16 at each step 18, 20, 22. The staircase structures with steps 18, 20, 22 provide different lengths for each layer of conductive layers 16. The conductive layers 16 will be formed into electrodes having different sizes in later steps.

Referring to FIG. 3, a dielectric material 26 is deposited over the staircase structures to rebuild the dielectric over the structure. The dielectric material 16 may include a same material as the dielectric layers 16. The dielectric material 26 covers the ends of the conductive layer 16 exposed during the formation of the staircase structure. The dielectric material 26 may be formed spinning from solution, spraying from solution, CVD, PECVD, sputter deposition, reactive sputter deposition, ion-beam deposition, evaporation, ALD, etc. After the deposition of the dielectric material 26, a planarization process, such as e.g., a chemical mechanical polishing (CMP) or an etch may be performed to level off a top surface of the device 10.

Referring to FIG. 4, contact openings 32 are patterned into the dielectric material 26 and the dielectric layers 14. The dielectric material 26 and the dielectric layers 14 will be referred to collectively from this point as dielectric material 26 for ease of reference. The contact openings 32 are formed about a central position or a centerline 25 of the conductors 16 so that a symmetrical structure is formed having contact openings 32 on either side of a centerline 25 (or other position) at each level. The contact openings 32 at each level are further apart from each other with depth (e.g., at the highest level the contacts openings 32 are closest together). While the staircase structure is illustratively depicted; others structures may also be employed, including portions of a staircase structure, conductive lines may extend in other directions than shown (e.g., into or out of the plane of the page), etc.

The contact openings 32 may be formed by lithographic patterning/etching. A resist may be formed with openings therein corresponding with the contact holes 32, and the contact holes 32 may be etched using a RIE process to form openings 32 and expose the conductors 16.

Referring to FIG. 5, contacts 34 are formed by depositing a conductive material, which may include a same material as the conductive layer or conductors 16. In one particularly useful embodiment, the conductors 34 include copper. After the deposition of the contacts 34, a CMP or etch process may be performed to level off a top surface. A diffusion barrier or liner (e.g., TiN, TaN, etc.) may be formed to line the contact holes before the formation of the contacts 34.

Figure 6:
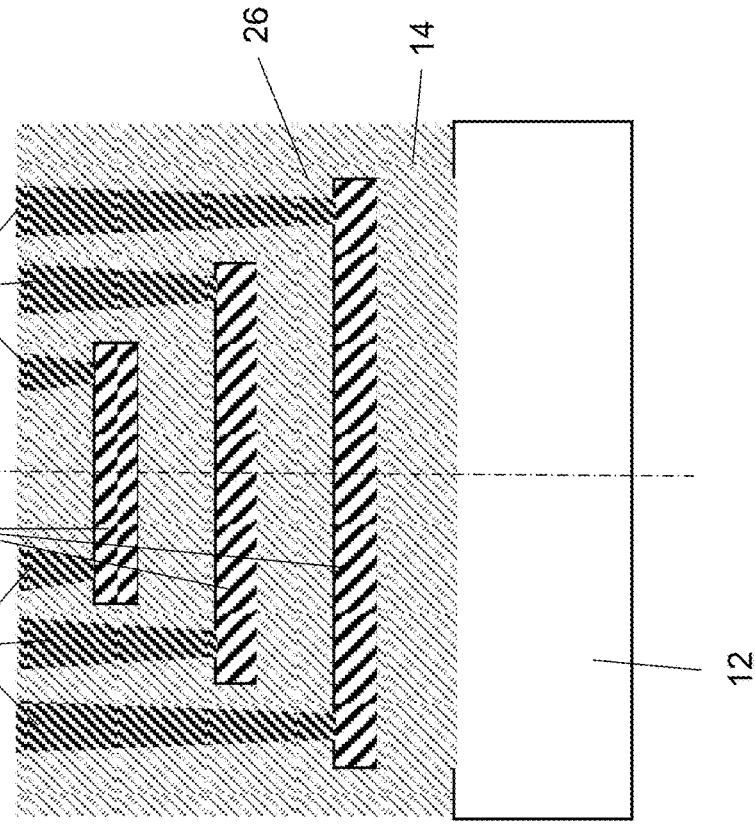
FIG. 6 is a cross-sectional view showing a nanopore formed through the dielectric layers and the conductive lines to form electrodes on opposite sides of the nanopore in accordance with the present principles.

Referring to FIG. 6, a nanopore 38 is formed down the centerline 25 (or other position) of the device 10. The nanopore 38 may be formed by a patterned etch (RIE), formed by a direct self-assembly process (DSA) for forming a mask followed by a RIE or formed by any other suitable pattern/etch process. The mask may be formed by a resist or by employing DSA materials. In one embodiment, a DSA material is formed in an opening located at the centerline. In one embodiment, the DSA material may include block copolymer (BCP), which may include poly(styrene)-b-poly (methyl methacrylate diblock copolymers (PS-b-PMMA)), poly(styrene)-block-poly(hydroxystyrene) diblock copolymers (PS-b-PHOST), polystyrene-b-poly lactic acid (PS-b-PLA) and/or other DSA materials. The DSA material may be spun onto the device 10 or may otherwise be dispensed to coat the surface.

The DSA material may include a cylinder or lamella of BCP formed in the centerline hole, which is graphoepitaxially driven to form a cup (of PS) and a cylinder (PMMA) within the cup.

The DSA material is subjected to an anneal process. The anneal process may include a temperature of about 150 to 300 degrees C. for between about 1 minute to 10 hours. The anneal process causes the micro-phase separation of the BCPs and forms nanoscale domains, e.g., cylinder and cup. In one embodiment, region (cylinder) includes PMMA material or PLA material, and the cup region includes PS material. Next, the cylinder is removed (by etching selective to the cup), and a bottom of the cup region is broken through by a selective etch process. This leaves an opening, which will be employed as an etch mask for opening up the layers 14 and 16 below.

The nanopore may include a thickness or diameter of between about 3 nm to about 40 nm depending on the applications. Other sized nanopores may also be employed. The nanopore 38 is etched through the layers 14 and 16 and stops on the substrate 12.

Referring to FIG. 7, a back channel 40 is formed by removing a portion of the substrate 12 to create a through passage for the nanopore 38. The back channel 40 may be formed by a patterned back-side etch of the substrate 12. The etch process is preferably selective to the other materials of the device 10. The back channel 40 dimensions may be customized as needed for the application. The etch process may include the use of lithographic patterning although any suitable technique may be employed. The configuration shown in FIG. 7 may be employed for characterizing molecules in accordance with the present principles. The molecules may include polymers, DNA, RNA, portions of RNA or DNA, proteins, viruses, etc.

Referring to FIG. 8, in accordance with another embodiment, a top surface is protected by a mask, and the nanopore 38 may be exposed to a wet or dry selective etch process. The etch process recesses the dielectric material 26 to expose a larger portion of the conductors 16. The etch exposes tips of the conductor 16 to enhance the electric fields. In particularly useful embodiments, the conductors 16 include nanowires, although narrow plates or fins may also be employed.

Referring to FIG. 9, a nanopore device 50 is shown having sharp conductive tips 52. The conductive tips 52 are separated by a distance of between about 0.5 nm and about 5 nm to permit a molecule 46 to fit therethrough. In each tip pair (e.g., tips 52 on either side of the nanopore 42), there is one tip 52 that is grounded (connected to ground 54) and the other tip 52 is biased (e.g., connected to a positive voltage (V+) line 56). When the molecule 46, e.g., DNA, passes the nanopore 42, the molecule 46 changes a tunneling current between the conductor tips 52 in each pair. In the case of DNA, different DNA nucleobases (nucleotides) cause different changes or effects in the tunneling current. Therefore, as the DNA molecule 46 passes through, a sequence of tunneling current changes are measured. This can be employed for determining the nucleobases in the sequence. The number of different tip pairs provides measurements and checks on the sequencing in a single pass of the molecule 46. The tunneling current of each nanopore layer (tip pair) is recorded. This is equivalent to sensing the DNA multiple times, but without having to reload and reorient the molecule 46, which could cause other issues (breaking or other degradation). The signals along the DNA molecule 46 may be averaged to minimize any variation due to the non-uniformity of the nanopore 42. This results in improved accuracy and a reduction in set up and measurement time.

Referring to FIG. 10, a top down view of one layer 60 of the nanopore sensor device 50 is shown in accordance with one illustrative embodiment. The single layer 60 shows a tip pair having tips 52 on opposing sides of the nanopore 42. The tips 52 are connected to the contacts 34 by conductors 16, which may include nanowires or other metallization structures. At each layer 60, two conductor nanowires form a pair of electrodes that serve as a sensor. The two electrodes (anode and cathode) are physically disconnected. When DNA or other molecule passes through the nanopore 42, it changes the tunneling current of each sensor.

Figure 11:
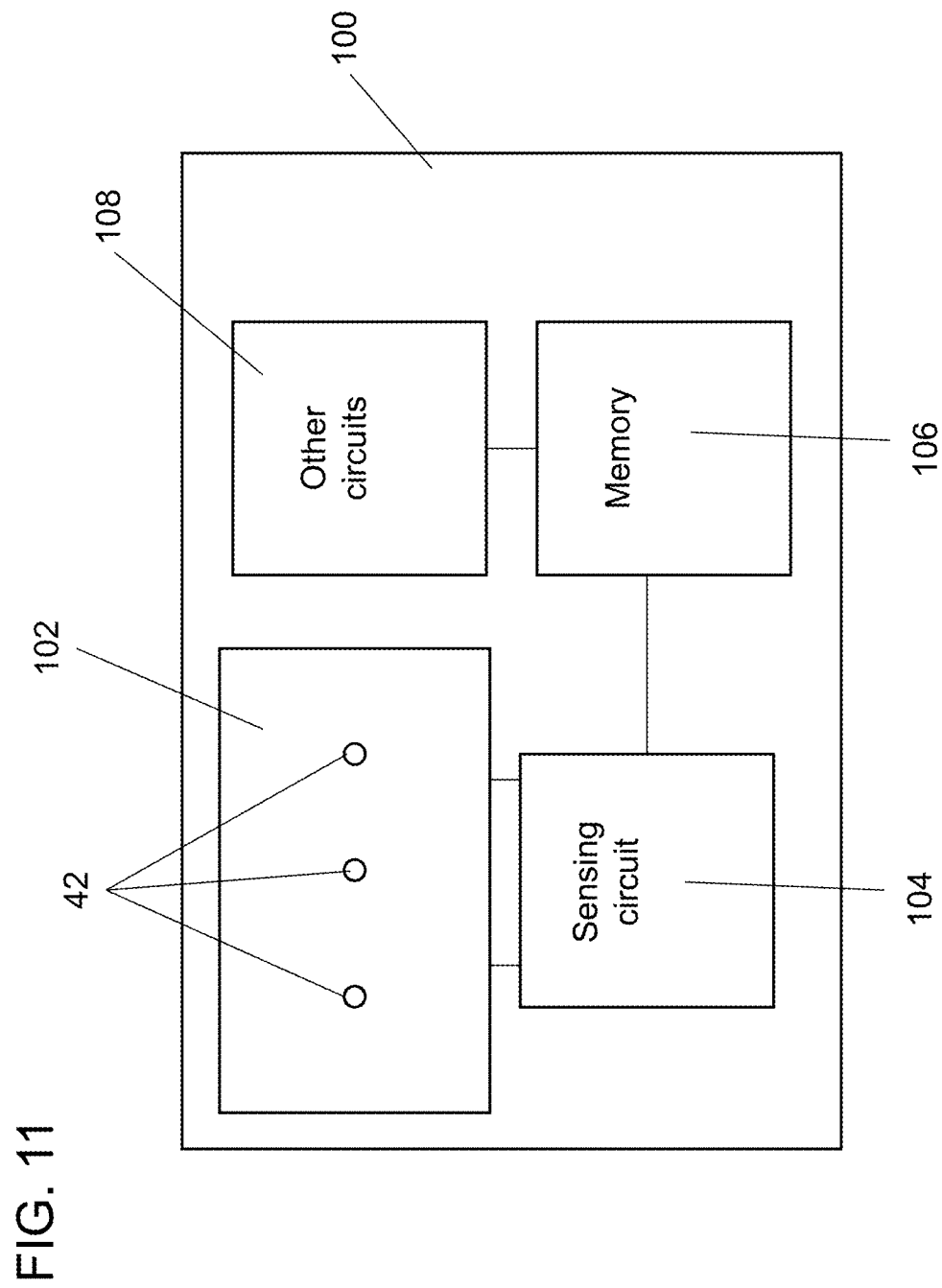
FIG. 11 is a schematic block diagram illustratively showing an integrated circuit having a stacked nanopore, a sensing circuit and memory in accordance with the present principles.

Referring to FIG. 11, a sensor device 100 may include an integrated circuit. The sensor device 100 may be an application specific integrated circuit (ASIC) or may be integrated into a standard chip or chips. The sensor device 100 may be formed on a wafer (the substrate 12) and diced to form a chip. The sensor device 100 may include a nanopore region 102 that may include one or more nanopores 42 formed therein. The nanopores 42 include connections such as contacts and electrodes employed for taking measurements and providing measurement signals to a sensing circuit 104. The sensing circuit 104 measures tunneling currents through molecules to characterize the materials between anode/cathode electrodes across the nanopore(s) 42. The sensing circuit 104 can recognize differences in the tunneling currents to be able to identify, e.g., a type of nucleobase of a DNA molecule.

While the present principles have been described in terms of a DNA molecule, it should be understood that the present principles are applicable to any suitable molecule. In particularly useful embodiments, the molecule is preferably elongated to pass through the nanopore and should be relatively electrically neutral. However, measurements may be made on any molecules, including but not limited to DNA, RNA, amino acids, proteins, viruses, etc.

The sensing circuit 104 connects to the pairs of sensors (e.g., tips 52 and/or conductors 16), which function as variable capacitors in one embodiment. Sensing current is measured by employing contacts 34 connected to other metallization structures (not shown) in the device 100. Sensing current is measured at several locations. The current measurements are stored in memory 106. The sequences may be stored in memory and compared for consistency. In one embodiment, the results are averaged to provide a better measure for the sequences. Depending on the material provided in the gap between the tips 52, the sensor circuit 104 measures the tunneling current across the sensor and stores the results in memory 106, which can be provided on-chip or off-chip. The electrical properties measured provide an indication of the type of nucleotide or complementary pairs of bases that are present between the electrodes (in the gap(s)).

The sensor device 100 may include other circuits 108 and functions as well. Logic, programmable features, analysis circuitry, etc. may be employed and formed on the device 100.

Figure 12:
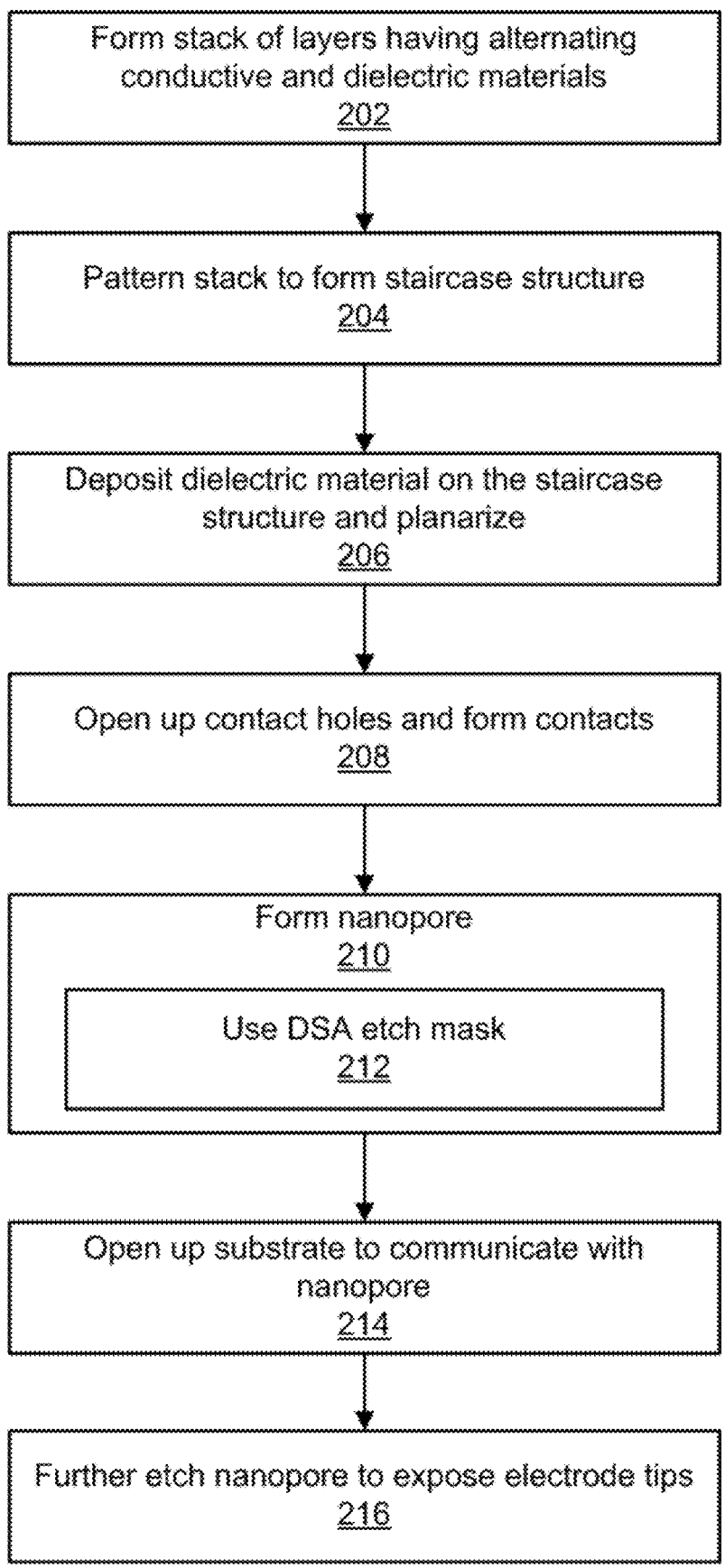
FIG. 12 is a block/flow diagram showing a method for fabricating a stacked nanopore in accordance with the present principles.

Referring to FIG. 12, a method for fabricating a stacked nanopore is shown in accordance with illustrative embodiments. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In block 202, a stack of layers having alternating conductive lines and dielectric layers are formed on a substrate. In one embodiment, the conductive lines may be patterned layers of conductive material. In other embodiments, the lines may be deposited or formed as nanowires or fins. The dielectric layers may include oxides or other suitable dielectric materials. Alternatively, the dielectric layers may be blanket deposited over the conductive lines.

In block 204, the stack is patterned to form a staircase structure with the conductive lines having a length gradually changing at each level in the stack. In one embodiment, the conductive lines are symmetric about a vertical centerline that extends normally to a main surface of the substrate.

In block 206, a dielectric material is deposited and planarized over the staircase structure. In block 208, contact holes are opened up and contacts are formed through the dielectric material landing on the conductive lines for each level of conductive lines. The contacts may also be symmetrical about the centerline. The contacts are formed on both sides of the center.

In block 210, a nanopore is etched through the stack of layers to form pairs of opposing electrodes across the nanopore using the conductive lines. In block 212, the nanopore may be etched using an etch mask formed by a directed self-assembly process, although lithography or other patterning processes may be employed. In block 214, the substrate is opened up to expose and fluidly communicate with the nanopore from a backside of the substrate.

In block 216, the nanopore may be further etched to recess the dielectric materials to expose the electrodes in the nanopore. Processing may continue with the formation of other components on the substrate.

Having described preferred embodiments for DNA sequencing with stacked nanopores (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A sensing device, comprising:
a stack of dielectric layers alternating with conductive layers where conductive materials are disposed between the dielectric layers;
a nanopore disposed through the stack of dielectric layers such that the nanopore severs the conductive layers into separate, disconnected tip pairs for each of the conductive layers, forming separate, disconnected electrodes from the conductive layers on opposite sides of the nanopore; and
contacts connecting to each of the electrodes.

2. The sensing device as recited in claim 1, wherein the conductive materials include conductive lines.

3. The sensing device as recited in claim 2, wherein the conductive lines form a staircase structure with a longest conductive line at a first level and shorter conductive lines at each successive level.

4. The sensing device as recited in claim 2, wherein the conductive lines include nanowires.

5. The sensing device as recited in claim 1, wherein the conductive lines have tips extending into the nanopore.

6. The sensing device as recited in claim 1, wherein the stack of dielectric layers is formed on a substrate.

7. The sensing device as recited in claim 6, wherein the substrate includes integrated circuitry.

8. The sensing device as recited in claim 7, wherein the integrated circuitry includes a sensor circuit to measure tunneling current differences when a molecule is present in the nanopore.

9. The sensing device as recited in claim 6, wherein the nanopore extends through the substrate.

10. The sensing device as recited in claim 1, wherein the electrodes on opposite sides of the nanopore form two or more electrode pairs, wherein each electrode pair forms a sensor for measuring tunneling current changes when a molecule is present between the electrodes.

11. A sensing device, comprising:
a stack of dielectric layers having conductive lines alternating between each of the dielectric layers, the stack of dielectric layers being formed on a substrate;
a nanopore disposed through the stack of dielectric layers such that the nanopore severs the conductive layers into separate, disconnected tip pairs for each of the conductive layers, forming separate, disconnected electrodes from the conductive layers on opposite sides of the nanopore, wherein the electrodes form two or more electrode pairs and each electrode pair foil is a sensor for measuring tunneling current changes when a molecule is present between the electrodes; and
contacts connecting to each of the electrodes.

12. The sensing device as recited in claim 11, wherein the conductive lines form a staircase structure with a longest conductive line at a first level and shorter conductive lines at each successive level.

13. The sensing device as recited in claim 11, wherein the conductive lines include nanowires.

14. The sensing device as recited in claim 11, wherein the substrate includes integrated circuitry.

15. The sensing device as recited in claim 14, wherein the integrated circuitry includes a sensor circuit to measure tunneling current differences when a molecule is present in the nanopore.

16. The sensing device as recited in claim 11, wherein the nanopore extends through the substrate.

17. The sensing device as recited in claim 11, wherein the electrodes extend into the nanopore.

18. The sensing device as recited in claim 1, further comprising a dielectric cover within which the stack and the contacts are situated.

19. The sensing device as recited in claim 1, wherein the conductive materials narrow towards the nanopore.

20. The sensing device as recited in claim 1, wherein the dielectric layers are formed of silicon containing materials.

\* \* \* \* \*